United States Patent
Ossman et al.

(10) Patent No.: US 7,697,142 B2
(45) Date of Patent: Apr. 13, 2010

(54) CALIBRATION METHOD FOR COMPENSATING FOR NON-UNIFORMITY ERRORS IN SENSORS MEASURING SPECULAR REFLECTION

(75) Inventors: Kenneth R. Ossman, Macedon, NY (US); R. Enrique Viturro, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 313 days.

(21) Appl. No.: 11/962,817

(22) Filed: Dec. 21, 2007

(65) Prior Publication Data

US 2009/0161111 A1 Jun. 25, 2009

(51) Int. Cl.
*G01N 21/00* (2006.01)
*G01B 9/08* (2006.01)
(52) U.S. Cl. ...................... 356/445; 356/392
(58) Field of Classification Search ......... 356/445–448, 356/392–394
See application file for complete search history.

(56) References Cited

U.S. PATENT DOCUMENTS

| 4,951,088 | A | 8/1990 | Bonvallet et al. |
| 5,162,874 | A | 11/1992 | Butler |
| 5,204,538 | A | 4/1993 | Genovese |
| 6,016,204 | A | 1/2000 | Budnik et al. |
| 6,351,308 | B1 * | 2/2002 | Mestha ........................ 356/402 |
| 6,462,821 | B1 | 10/2002 | Borton et al. |
| 6,526,240 | B1 | 2/2003 | Pham et al. |
| 7,259,857 | B2 | 8/2007 | Butterfield et al. |
| 7,439,491 | B2 * | 10/2008 | Xu et al. ..................... 250/234 |
| 2006/0024077 | A1 | 2/2006 | Scheuer et al. |
| 2006/0153580 | A1 | 7/2006 | Mo et al. |
| 2009/0040261 | A1 * | 2/2009 | Zhang et al. ................... 347/19 |

* cited by examiner

*Primary Examiner*—Michael P Stafira
(74) *Attorney, Agent, or Firm*—Pillsbury Winthrop Shaw Pittman LLP

(57) ABSTRACT

This invention relates to a method for the calibration of linear array photo sensors operating in a specular reflection mode. Errors may be introduced when a highly diffused image is measured by the linear array photosensor that was calibrated in a specular mode. These errors result in artifacts such as streaks in the captured image. The method measures non-uniformity errors using a highly diffuse white reflective surface, and then applies an appropriate scaled pixel-wise correction factor to the image when the sensor is used in the specular mode.

16 Claims, 7 Drawing Sheets

AC=100%

AC=50%

CALIBRATION METHOD FOR COMPENSATING FOR NON-UNIFORMITY ERRORS IN SENSORS MEASURING SPECULAR REFLECTION

FIELD

This present application relates to a method for calibrating sensors operating in a specular reflection mode.

BACKGROUND

In conventional marking systems, such as, for example, a laser printer, inkjet printer, or copier, one technique for monitoring the quality of images is to create one or more "reference" or "test" patches of pre-determined desired tint. The reference/tint of a test patch may be referred to as the call or the density of the reference/test patch. The actual density of the material (often ink and/or toner) in each test patch can then be measured to determine the effectiveness of the printing process on marking a medium, such as for example, a reference strip on a photoreceptor or intermediate medium. The uniformity of the image on the reference strip can then be determined.

It is known that non-uniformity in the appearance of printed materials intended to be uniform is a persistent problem for marking technologies, such as direct-digital production color technologies. Thus, marking machines have inherent error manifesting itself in residual non-uniformities, even after all normal service actions, such as machine self-check diagnostics and technician implemented procedures, have been performed on a marking machine. These residual non-uniformities may occur, for instance, where an image to be printed is intended to be a specific uniform tone, but shows areas which are lighter or darker, or a different tone than other areas. These different areas of the same image are variations that were not intended when the image data was generated and do not reflect the image data generated. The ability to assess and diagnose unwanted non-uniformity is a problem for field service personnel. Engineering tools such as densitometers, two-dimensional precision color scanners, digital cameras, flat bed cameras, and elaborate signal processing which may be available in the lab are generally unavailable to field service personnel who must use simpler and less capable tools. Generally, field personnel must use printed standard image references (SIR) and visual comparisons to determine whether a printing system meets its specified uniformity performance. Additional transparent overlays are placed on printed images to determine spatial frequencies of unwanted image bands. The processes are subjective and thus, have a tendency to be inaccurate.

In the case of xerographic devices, such as a laser printer, the surface that is typically of most interest in determining the density of printing material thereon is the charge-retentive surface or photoreceptor, on which the electrostatic latent image is formed and subsequently developed by causing toner particles to adhere to areas thereof that are charged in a particular way. There is typically a routine within the operating system of the printer to periodically create test patches of a desired density at predetermined locations on the photoreceptor by deliberately causing the exposure system thereof to charge or discharge as necessary the surface at the location to a predetermined extent. Test patches are used to measure the deposition of toner on paper to measure and control the tone reproduction curve.

The test patch is then moved past the developer unit and the toner particles within the developer unit are caused to adhere to the test patch electrostatically. The denser the toner on the test patch, the darker the test patch will appear in optical testing. The developed test patch is moved past a light sensing device disposed along the path of the photoreceptor, and the light absorption of the test patch is tested; the more light that is absorbed by the test patch, the denser the toner on the test patch. The sensor readings are then used to make suitable adjustments to the system such as changing developer bias to maintain consistent quality.

Typically each patch is about an inch in the process direction and extending the full width across the process that is printed as a uniform solid half tone or background area. This practice enables the sensor to read one value on the tone reproduction curve for each test patch.

Often, however, when a full-width array sensor module that uses a lens array for imaging captures images in specular reflecting mode, spatially localized non-uniformities of the sensor response are seen. When these same types of sensors are used in a diffuse mode they also exhibit non-uniformities but they are not the same size or in the same locations along the array width. Normal calibration techniques of dark offset and gain correction eliminate almost all effects of these non-uniformity errors when the sensor is used to measure the reflectance of inks or toners that are very light-absorbing.

However, if the material being imaged has a significant high diffuse reflectivity and the sensor is being used in a predominantly specular reflecting mode, then the difference of the two non-uniformities shows up uncorrected in the images. This may result in artifacts such as narrow point streaks during the image processing and subsequent bitmap manipulation.

SUMMARY

A method for eliminating non-uniformity errors of this type is provided.

In one embodiment, a method for calibrating a specular reflectance measurement sensor for use in a device, is provided, comprising: providing a sensor module, the sensor module comprising: (i) an illuminator configured to emit a beam of light at a target, thereby producing specular reflectance at an angle; (ii) a linear array sensor configured to detect that specular reflectance; and (iii) a processor configured to process the specular reflectance detected by the sensor; measuring a reflectance profile of a diffuse white reflecting surface using the sensor module and storing it in a memory; determining a non-uniformity correction factor which quantifies reflectance non-uniformity differences between a target and the diffuse white reflecting surface; measuring a specular reflectance profile of a target using the sensor module; determining a calibrated specular reflectance profile of the target based upon the pixel-wise non-uniformity correction factor, and providing the calibrated specular reflectance profile of the target to the device.

In another embodiment, a computer readable media having stored computer executable instructions, wherein the computer executable instructions, when executed by a computer, directs a computer to perform the above method for calibrating a specular reflectance measurement sensor for use in a device.

Other objects, features, and advantages of one or more embodiments of the present disclosure will seem apparent from the following detailed description, and accompanying drawings, and the appended claims.

BRIEF DESCRIPTION OF THE DRAWINGS

Embodiments will now be disclosed, by way of example only, with reference to the accompanying schematic drawings in which corresponding reference symbols indicate corresponding parts, in which.

DETAILED DESCRIPTION OF INVENTION

Figure 1:
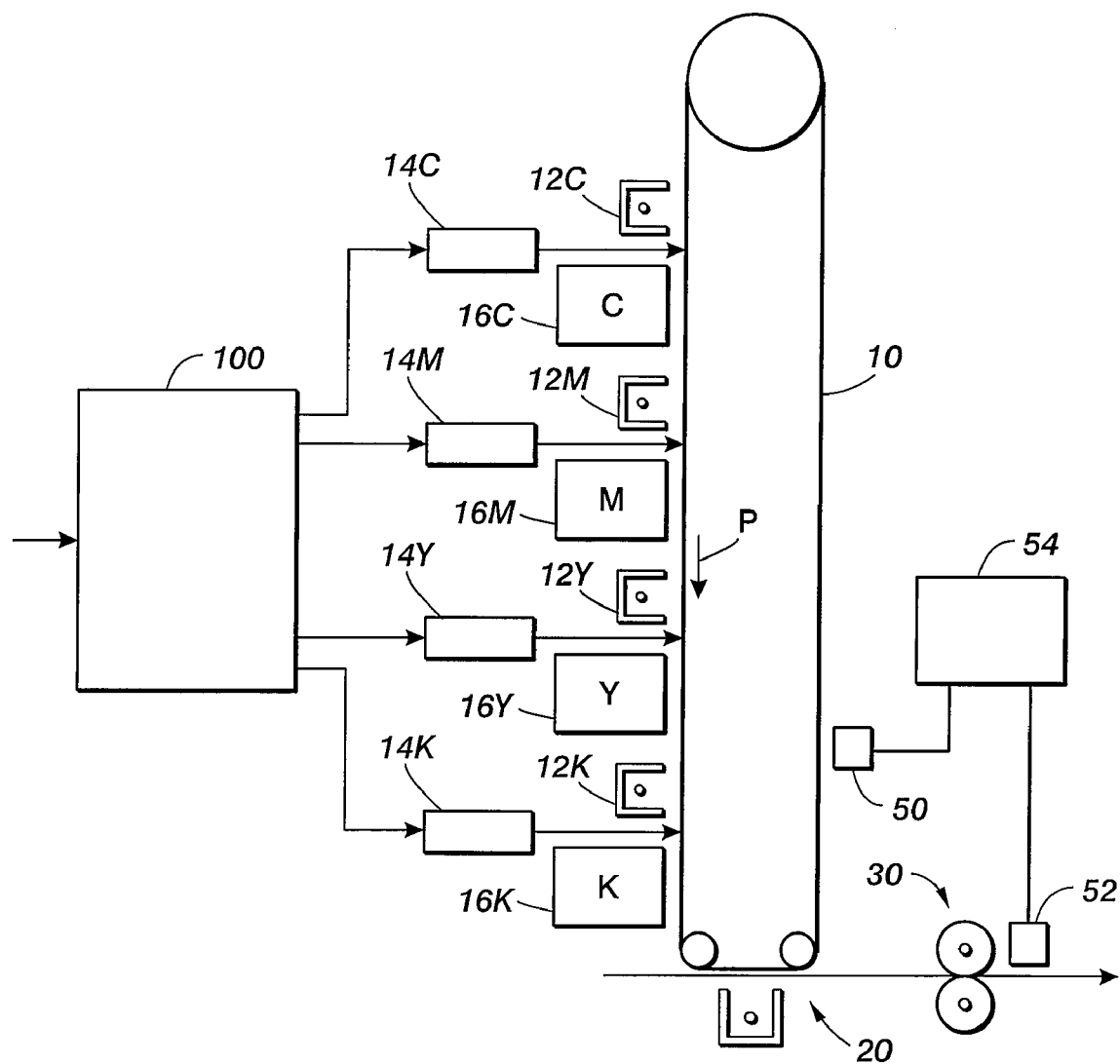
FIG. 1 is a simplified elevational view of basic elements of a color printer, showing a context.

FIG. 1 is a simplified elevational view of the basic elements of a color printer, showing a context for the present application. Specifically, there is shown an "image-on-image" xerographic color printer, in which successive primary-color images are accumulated on a photoreceptor belt, and the accumulated superimposed images are in one step directly transferred to an output sheet as a full-color image. In one implementation, the Xerox Corporation iGen3® digital printing press may be utilized. However, it is appreciated that any printing machine, such as monochrome machines using any technology, machines which print on photosensitive substrates, xerographic machines with multiple photoreceptors, or ink-jet-based machines, can beneficially use embodiments of the present application as well.

Specifically, the FIG. 1 embodiment includes a belt photoreceptor 10, along which are disposed a series of stations, as is generally familiar in the art of xerography, one set for each primary color to be printed. For instance, to place a cyan color separation image on photoreceptor 10, there is used a electrostatic charge device (e.g., a corotron) 12C, an imaging laser 14C, and a development unit 16C. For successive color separations, there is provided equivalent elements 12M, 14M, 16M (for magenta), 12Y, 14Y, 16Y (for yellow), and 12K, 14K, 16K (for black). The successive color separations are built up in a superimposed manner on the surface of photoreceptor 10, and then the combined full-color image is transferred at transfer station 20 to an output sheet. The output sheet is then run through a fuser 30, as is familiar in xerography.

Also shown in the FIG. 1 are sensors 50 and 52, which can feed back to a control device 54. The sensors such as 50 and 52 are devices which can make measurements to images created on the photoreceptor 10 (such as sensor 50) or to images which were transferred to an output sheet (such as sensor 52). These sensors can be in the form of optical densitometers, colorimeters, electrostatic voltmeters, etc. There may be provided any number of sensors, and they may be placed anywhere in the printer as needed, not only in the locations illustrated. The information gathered therefrom is used by control device 54 in various ways to aid in the operation of the printer, whether in a real-time feedback loop, an offline calibration process, a registration system, etc.

Typically, a printer using control systems which rely on sensors such as 50, 52 require the deliberate creation of what shall be here generally called "test patches" which are made and subsequently measured in various ways by one or another sensor. These test patches may be in the form of test marks of a predetermined darkness value, a predetermined color blend, or a particular shape, such as a line pattern; or they may be of a shape particularly useful for determining registration of superimposed images ("fiducial" or "registration" marks). Various image-quality systems, at various times, will require test marks of specific types to be placed on photoreceptor 10 at specific locations. These test marks will be made on photoreceptor 10 by one or more lasers such as 14C, 14M, 14Y, and 14K. Printing process may be controlled, for example, by a print controller 100.

As is familiar in the art of "laser printing," by coordinating the modulation of the various lasers with the motion of photoreceptor 10 and other hardware (such as rotating mirrors, etc., not shown), the lasers discharge areas on photoreceptor 10 to create the desired test marks, particularly after these areas are developed by their respective development units 16C, 16M, 16Y, 16K. The test marks are placed on the photoreceptor 10 in locations where they can be subsequently measured by a (typically fixed) sensor elsewhere in the printer, for whatever purpose.

The density of toner deposits may be controlled using a reflectivity control system. For example, a Compact Image Sensor (CIS) module is one type of sensor 50, 52 for measuring toner reflectivity on the photoreceptor and providing feedback to the print controller 100.

Figure 2:
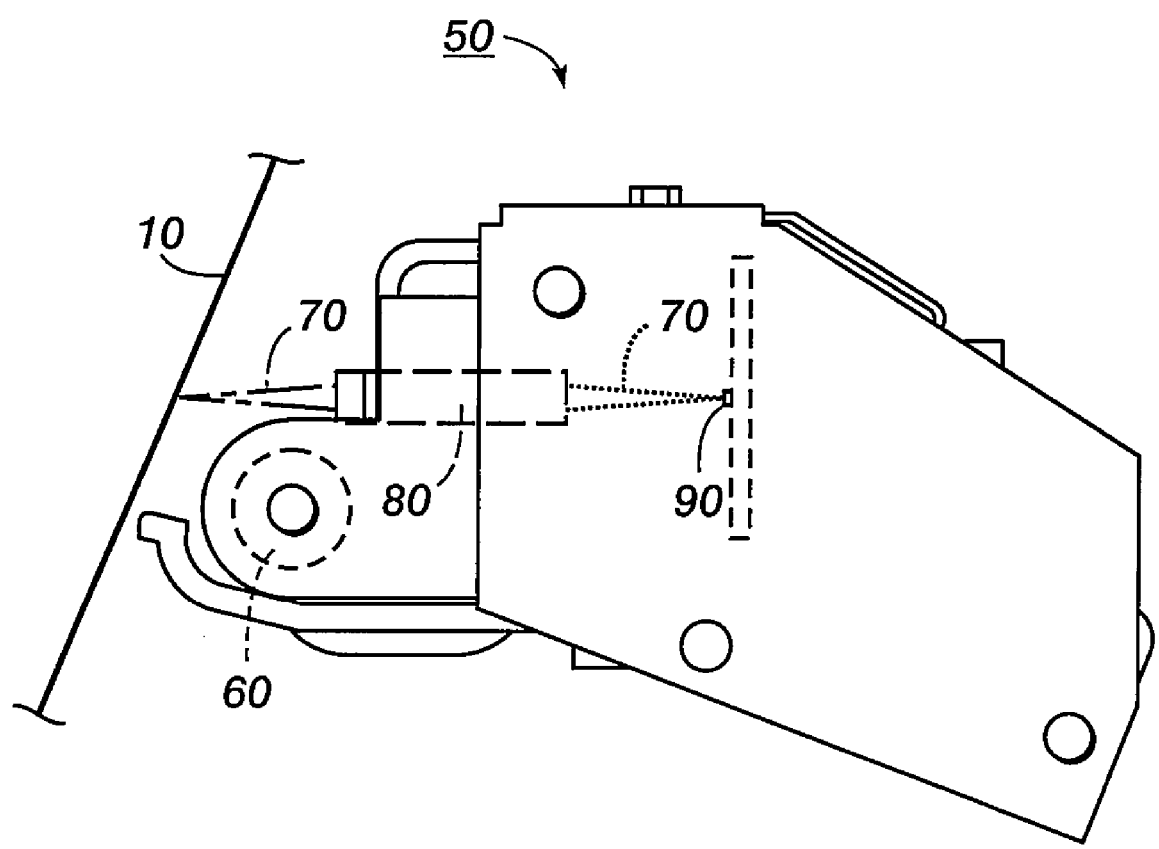
FIG. 2 shows an exemplary Compact Image Sensor (CIS) module, according to an embodiment.

FIG. 2 shows an exemplary Compact Image Sensor (CIS) module, according to an embodiment. While reference herein is made to a CIS module, it will be appreciated that any optical sensor may be used, such as densitometers, colorimeters, cameras, photosensors, or the like. The CIS module 50 may include an illuminator 60 for providing light to a photoreceptor belt 10. The light 70 reflected off the photoreceptor 10 passes through a lens 80, and is detected by a photosensor 90 with associated electronic drivers. In one implementation, the lens may be a SELFOC™ lens array, manufactured by NSG America, Inc., the illuminator 60 may be a fluorescent lamp and the photosensor 90 may be a butted linear array of 600 dpi photosensitive elements to provide a full-width array sensor.

The photoreceptor belt has a mirror-like surface, which is highly specular. Thus, the reflectivity of the photoreceptor is very high and appear bright to the sensor so that its value can be set as the reference. Toner on the other hand may be diffusely reflective. A test patch of toner may developed on the photoreceptor and its reflectance sensed and compared to a reference stored in a memory. The difference between the known stored reflectance of the test patch and the reflectivity of the test patch measured in situ may be used to control the proper toner concentration. Thus, if the measured reflectance varies form the stored predetermined value, a corrections to the toner application may be made.

Generally all CIS modules have inherent non-uniform responses along their width due to variability of illumination, chip and pixel dark offset, and chip and pixel gain. The known method is to first perform a in vitro calibration process for each sensor. This method includes capturing and storing the pixel-wise reflectance profile of the photoreceptor having no light thereupon it, known as a DARK reflectance profile, and then capturing and storing the pixel-wise reflectance response to a very uniform white target surface, known as a WHITE reflectance profile. The WHITE and DARK reflectance profiles are retained in a long term memory for later use on every new image captured, known as a SAMPLE reflectance profile. In particular, these measurements readings may be made for calibrated test patches. When an image is taken of any target, a sample specular reflectance profile, $R_W$ is applied in an attempt to correct for the non-uniformities within the printing machine, according to Equation 1, as follows:

$$R_W(i) = [\text{SAMPLE}(i) - \text{DARK}(i)] / [\text{WHITE}(i) - \text{DARK}(i)] \quad (1)$$

In the Xerox Corporation iGen3® digital printing press, the CIS module 50 is mounted at approximately a 22.5 degree angle with respect to the photoreceptor 10 and thus, it operates with a large proportion of specular reflected light from the photoreceptor 10.

The same calibration technique according to Equation 1 may also be used to correct the same types of non-uniformity errors, where the bare photoreceptor surface is treated as the "WHITE" reference. Thus, the pixel-wise reflectance profile response from a bare photoreceptor, known as a PR reflectance profile may be substituted for the WHITE reflectance profile in Equation 1. The image measurement of the SAMPLE reflectance profile may be taken, using the CIS module 50, within the printing machine.

Next, a specular reflectance profile for a sample on the photoreceptor, $R_{PR}(i)$ may be calculated based on the SAMPLE reflectance profile, so as to produce a linear reflectance response result from the corrected dark offset and gain, according to Equation 2, as follows:

$$R_{PR}(i) = [\text{SAMPLE}(i) - \text{DARK}(i)] / [PR(i) - \text{DARK}(i)] \quad (2)$$

Figure 3:
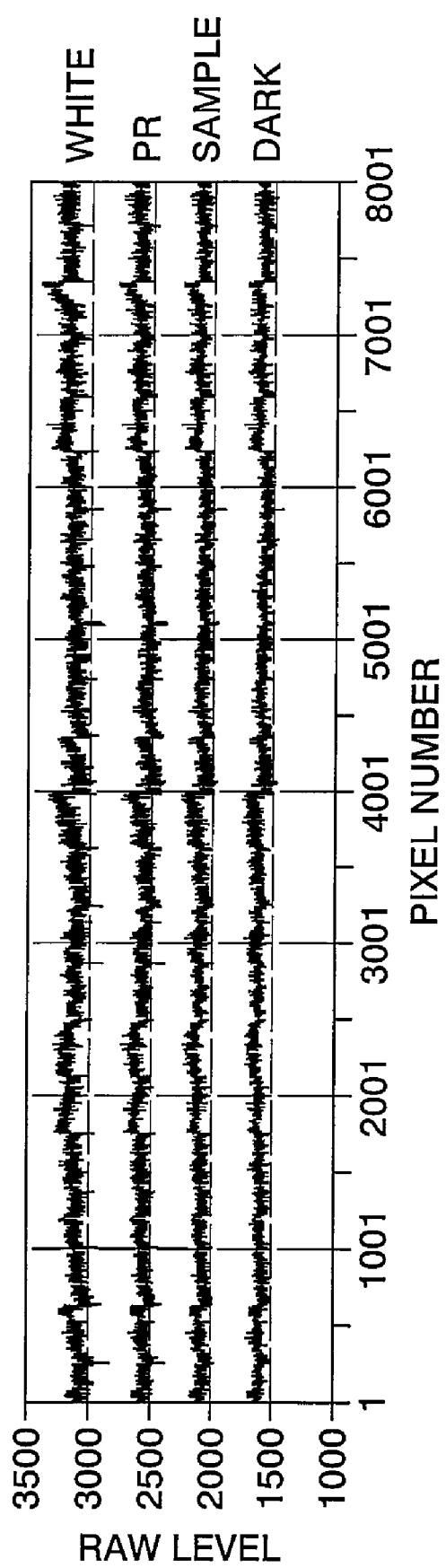
FIG. 3 shows typical raw response reflectance profiles for DARK, PR, WHITE and SAMPLE.

FIG. 3 shows typical raw response reflectance profiles for DARK, PR, and WHITE captured for each pixel, i of photosensor, as well as for the SAMPLE reflectance profile. All raw response values may be, for example, in units of voltage (e.g., microvolts), as returned from the CIS module 50, 52.

A problem occurs, however, due to unfused color toners reflecting in a diffuse mode and misalignment of SELFOC™ lens elements, which result in small localized regions of the lens array having different angles of acceptance of incoming light. Thus, the narrow fan of rays available to the lens element in the specular mode has a different sensor response signature than a wide angular fan off the diffuse surfaces.

Figure 4:
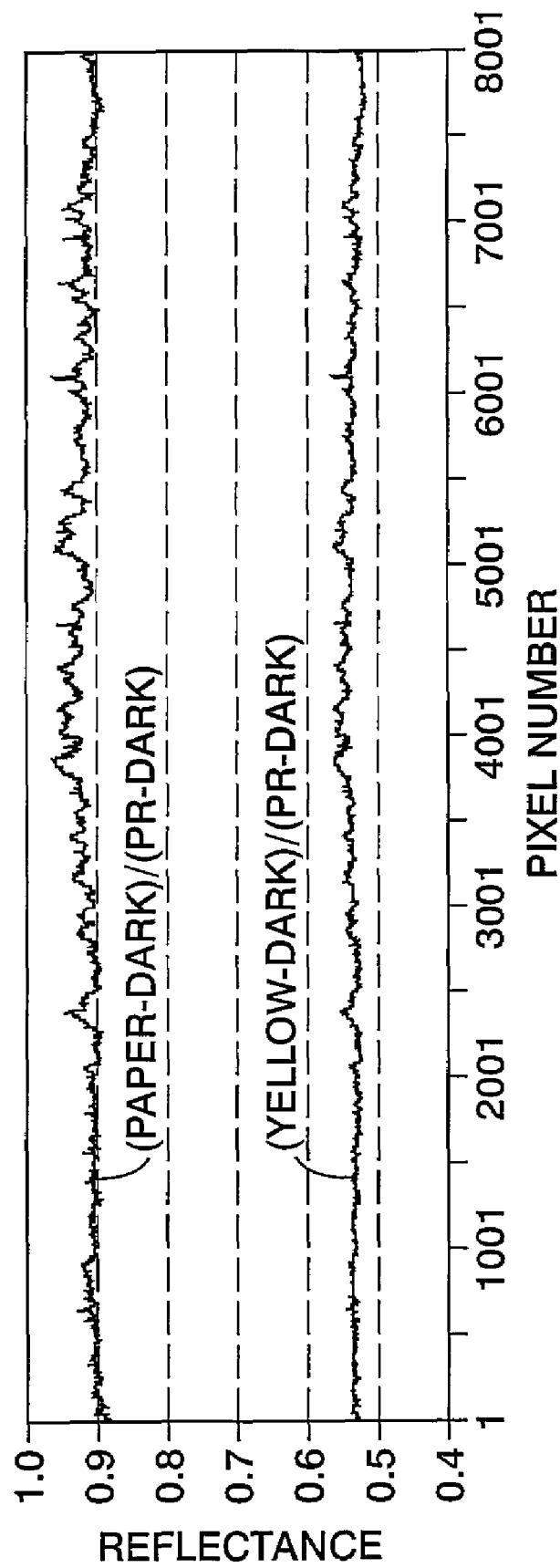
FIG. 4 shows scaled reflectance profiles for an ordinary piece of white paper and for a solid area test patch of yellow toner on the photoreceptor.

FIG. 4 illustrates this phenomenon. For example, the scaled reflectances for an ordinary piece of white paper and for a solid area test patch of yellow toner on the photoreceptor, are shown. There is a relatively tight correlation between errors in both plots. As is apparent, both of the reflectance profiles include many peaks and valleys at approximately the same pixel locations of the photosensor array, regardless of whether the target surface was paper or the toner. These narrow non-uniformities are due to the geometry of the reflecting angles, much more than due to the small surface irregularities of the calibrating photoreceptor medium.

In light of the fact that these non-uniformity errors are built into the lenses of the sensor, which have a characteristic signature, a correction method is proposed.

First, the photosensor is used to capture a reflectance profile of a high-quality diffuse white reflecting surface in a specular mode, known as a WHITE reflectance profile, during an in vitro calibration procedure (also known as a "bench correction"). The calibration procedure is referred to as an in vitro calibration, because it is performed prior to the sensor being installed in the printing machine.

In one implementation, the diffuse white reflecting surface may be, for example, a white polycarbonate resin sheet (e.g., Lexan®) or a high quality sheet of white paper.

The in vitro measured pixel-wise WHITE reflectance profile may be stored in a memory within the CIS module or in the printing machine and later used for subsequent calibration in the printing machine in situ (i.e., after the sensor has been installed in the printing machine). In one implementation, the WHITE reflectance profile may be determined during the manufacturing process of the CIS module. For example, it may be performed during a calibration step in the manufacturing process-line. In other implementations, the WHITE reflectance profile may be recalibrated after the CIS module is installed within the printing machine (through the machine's calibration routine), or the CIS module may be removed from the printing machine for recalibration.

When the WHITE reflectance profile is later calibrated for gain using the photoreceptor reflectance profile PR as a reference (for example, according to Equation 3, below) the resulting image profile may be used for compensating for the diffuse difference signature due to the non-uniformity of response. This unique pixel-wise profile can be stored in the memory of the CIS module and used as the basis for a correction factor to be applied to each image having a highly diffuse reflection content.

Another effect to be taken into account is the difference in illumination uniformity between the in vitro calibration measurement and actual measurements of real targets using the CIS module within the printing machine in situ. Both illumination intensity non-uniformity, as seen by the photosensor, and the specular signature error are dependent on distance and angle of incidence. The size of peaks or valleys and/or amplitude specular error signature will change with only small changes of mounting angles or defocus distances. However, non-uniformities due to mounting conditions are not observed in the in vitro calibration measurement of the diffuse white target. Only gross illumination fall-off due to distance may be seen in the in vitro measurement.

In fact, the differences between the specular and diffuse uniformity (i.e., the specular signature error) are only found after the CIS module has been installed in the printing machine. By contrast, the WHITE reflectance profile (which is stored in the memory of the CIS module or the printing machine) remains generally unaffected, even after the installation of the CIS module within the printing machine.

Since the WHITE reflectance profile is determined by an in vitro measurement, it may need to be rescaled with respect to the photoreceptor profile of the actual printing machine in situ. In one implementation, the specular reflectance profile for a sample on the photoreceptor, $R_{PR}$, according to Equation 2, may be normalized to the same mean intensity of the mean value of the WHITE reflectance profile, $\overline{\text{WHITE}}$ (see Equation 3A) when scaled to be equal to the mean value of the photoreceptor profile, $\overline{PR}$ (see Equation 3B). The scaled White reflectance profile, $R^W_{PR}$ may be calculated according to Equation 3, as follows:

$$R^W_{PR}(i) = [\text{WHITE}(i) - \text{DARK}(i)] / [PR(i) - \text{DARK}(i)] \times \frac{\overline{PR}}{\overline{\text{WHITE}}} \quad (3)$$

where:

$$\overline{\text{WHITE}} = \frac{1}{n} \cdot \sum_{i=1}^{n} \text{WHITE}(i); \quad (3A)$$

$$\overline{PR} = \frac{1}{n} \cdot \sum_{i=1}^{n} PR(i); \text{ and} \quad (3B)$$

n is the number of pixels.

$R^W_{PR}$ may then be used within the printing machine in situ to emulate the in vitro WHITE reflectance response of Equation 1. A pixel-wise non-uniformity correction factor, $\delta R_W$ which quantifies the reflectance non-uniformity differences between images of the photoreceptor surface and the diffuse white reflecting surface can be defined, according to Equation 4, as follows:

$$\delta R_W(i) = 1 - R^W_{PR}(i) \quad (4)$$

Application of this non-uniformity correction factor, $\delta R_W$ is directly proportional to the amount of diffuse reflecting content varying with the target.

However, the correction factor may use appropriate scaling factors based on the actual diffuse portion of the reflected light for a particular image measured by the photosensor in specular mode. In one implementation, the diffuse proportion of the light reflected from the photoreceptor to any pixel i of the photosensor may be derived from knowledge of toner area coverage, AC of the photoreceptor per unit halftone cell and the mean solid area reflectivity for a particular toner color c of a color scheme. Various color schemes may be employed, such as CMYK or RGB. In addition, a grayscale (single color) index may also be applied.

The toner area coverage, AC is defined as the percentage of toner area covering the unit halftone cell in the sample target that is available to reflect. Test patches may be formed in inter-document or inter-page zones of the photoreceptor belt using a calibration procedure having a desired toner area coverage, for example, as disclosed in U.S. Pat. No. 6,016,204, incorporated by reference herein, in its entirety.

Figure 5A:
FIGS. 5A and 5B illustrate exemplary test patches.
Figure 5B:
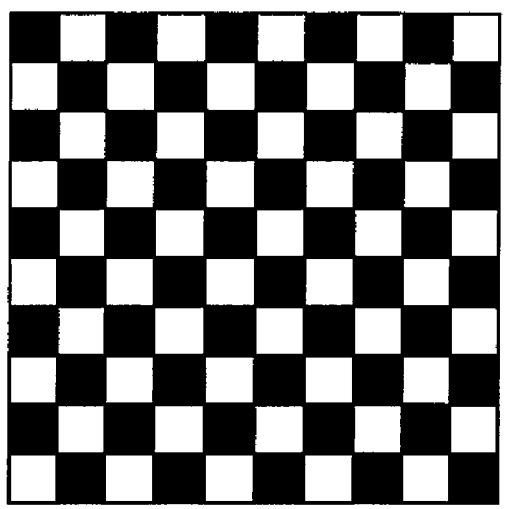

FIGS. 5A and 5B illustrate exemplary test patches. The test patches may be, for example, a 1 inch-square. However, it will be appreciated that any size test patch may be utilized. The coordinated system and specific imagable area for the test patch may be provided by the calibration phase. The toner area coverage AC may be varied uniformly for each test patch from 0 to 100%.

In FIG. 5A, the entire area of the test patch is completely covered in toner. Thus, for this particular test patch the toner area coverage, AC is 100%, and is consider to be a "solid area." FIG. 5B illustrates a halftone test patch having only approximately one-half of the area of the halftone cell covered by toner. Its toner area coverage AC is 50%. In this particular embodiment, the toner is uniformly distributed over the halftone cell area in a 10×10 "checker-board" pattern. While square halftone "dots" are illustrated in FIG. 5B, it will be appreciated that any halftone cell design may be used, for example, including dots or pixels which are circular, rectangular, triangular, etc, in various patterns.

$R_S^C$ provides a pixel-wise reflectance profile measurement in situ of the reflectivity of a solid area toner patch of a particular toner color C. In order to measure $R_S^C$, a number of solid area test patches, one for each toner color of the color scheme, for example, like the solid area test patch shown in FIG. 5A may be generated during a calibration phase of the printing machine. $R_S^C$ may be determined according to Equation 2, where the SAMPLE reflectance profile is a measurement of a reflectance profile for the solid area test patch.

The mean solid area color reflectivity $\overline{R_S^C}$ for that color of toner may be then calculated according to Equation 5, as follows:

$$\overline{R_S^C} = \frac{1}{n} \cdot \sum_{i=1}^{n} R_S^C(i) \quad (5)$$

where n is the number of pixels in the photosensor.

Further, a measure of the reflectivity of a particular test patch, $R_{AC}^C$ identifies the reflectivity due to the amount of toner covering the photoreceptor PR per unit halftone cell. This may be used as a good approximation of the diffuse and specular content at any pixel i located within that halftone cell, as long as the halftone cell size is not substantially larger than a sampling pixel.

To measure $R_{AC}^C$, a number of test patches of a desired toner area coverage AC, one for each toner color, for example, like the halftone cell shown in FIG. 5B, may be generated during a calibration procedure, as disclosed, for example, in U.S. Pat. No. 6,016,204, mentioned above. The average toner area coverage AC may be varied from 0 to 100%. In one implementation, a 50% halftone is used. $R_{AC}^C$ may be determined according to Equation 2, where the SAMPLE profile is a measurement of specular reflectance profile for the halftone.

The mean reflectance for the measured halftone cell $\overline{R_{AC}^C}$ then may be calculated according to Equation 6, as follows:

$$\overline{R_{AC}^C} = \frac{1}{n} \cdot \sum_{i=1}^{n} R_{AC}^C(i) \quad (6)$$

where n is the number of pixels in the photosensor.

Next, the ratio of diffuse light to specular light, DSR that is received by the photosensor may be determined. The diffuse to specular ratio DSR is defined as the mean halftone reflectance contrast for a particular toner color c divided by the mean reflectance contrast of a solid area of the same color, according to Equation 7, as follows:

$$DSR^C = \frac{1 - \overline{R_{AC}^C}}{1 - \overline{R_S^C}} \quad (7)$$

In another implementation, the value of DSR may also be approximated without measurement based on prior knowledge of the halftone cell structures alone. For example, both the measured values of $\overline{R_S^C}$ and $\overline{R_{AC}^C}$ are influenced by the variability of the tone reproduction curve (TRC) within the printing machine. When the printing machine is manufactured, the basic TRC has already been defined, and thus, the DSR may be determined based on knowledge from the TRC.

Now, the non-uniformity reflectivity error correction factor, $\delta R_W$ may be scaled based on the diffuse component of the reflected light from a halftone cell for a particular toner color C. The scaled non-uniformity reflectivity error correction factor, $\delta R_{AC}^C$ may be calculated, according to Equation 8, as follows:

$$\delta R_{AC}^C(i) = DSR^C \times \overline{R_S^C} \times \delta R_W(i) \quad (8)$$

Figure 6:
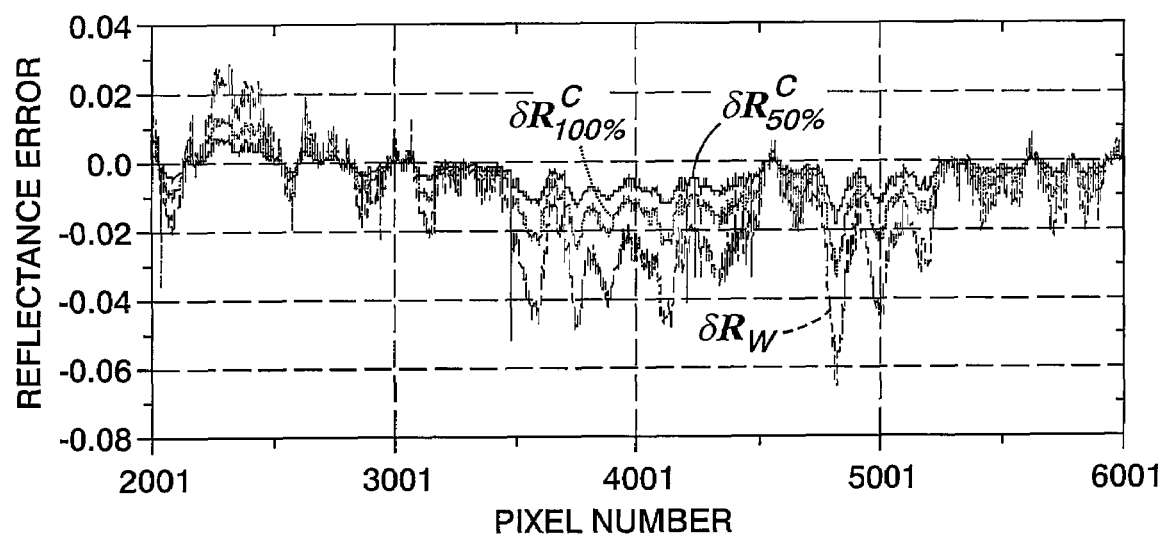
FIG. 6 shows a plot of the pixel-wise reflectance error correction profiles, over a selected portion of the width of the photosensor, for the diffuse white reflecting surface, $\delta R_W$ the solid area patch, $\delta R_{100\%}^C$ and the 50% halftone $\delta R_{50\%}^C$, respectively using the sampled test patches from FIGS. 5A and 5B.

FIG. 6 shows a plot of the pixel-wise reflectance error correction profiles, over a selected portion of the width of the photosensor, for the diffuse white reflecting surface, $\delta R_W$, the solid area patch, $\delta R_{100\%}^C$ and the 50% halftone $\delta R_{50\%}^C$, respectively using the sampled test patches from FIGS. 5A and 5B. As apparent from the plot, the in vitro correction factor $\delta R_W$ has been scaled, pixel-by-pixel, for both test patches, accordingly. The plot for the 50% halftone $R_{50\%}^C$ has a smaller diffuse reflectance error, at any given pixel i than the solid area patch $\delta R_{100\%}^C$. This is because the 50% halftone has one half of its area not covered in toner it has a greater a reflectance, compared to the solid area patch. As such, the diffuse reflectance error for the 50% halftone is also greater.

The scaled non-uniformity reflectivity error correction factor may now be applied to the specular reflectance, $R_m^C$ for any target. $R_m^C$ may be determined with respect to the photoreceptor, according to Equation 2. In one implementation the target may be a test patch, such that $R_m^C(i)=R_{AC}^C(i)$.

Lastly, a pixel-wise calibrated specular reflectance profile for a sample may be determined with respect to a measured reflectance profile according to Equation 9, as follows:

$$R'^C_m(i) = R_m^C(i) \times [1 + \delta R_{AC}^C(i)] \quad (9)$$

Figure 7:
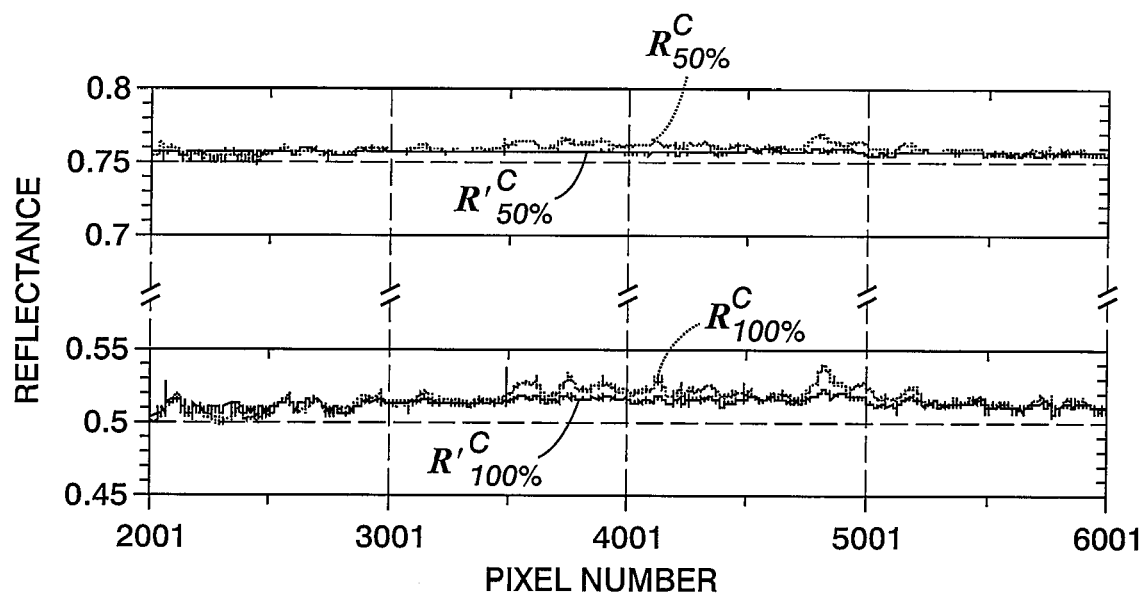
FIG. 7 shows the original uncorrected reflectance profiles, over a portion of the width of the photosensor, for the solid area patch $R_{100\%}^C$ and the 50% halftone $R_{50\%}^C$ similar to FIGS. 5A and 5B, respectively, and their corrected reflectances profiles, $R'_{100\%}^C$ and $R'_{50\%}^C$.

FIG. 7 shows the original uncorrected reflectance profiles, over a selected portion of the width of the photosensor, for the solid area patch $R_{100\%}^C$ and the 50% halftone $R_{50\%}^C$ similar to FIGS. 5A and 5B, respectively, and their corrected reflectance profiles, $R'^C_{100\%}$ and $R'^C_{50\%}$ as determined according to Equation 9. It is apparent from the plots that the pixel-wise correction, is effective in flattening-out and smoothing the peaks and valleys for the reflectance profiles for both the solid area patch and halftone, which are due to the non-uniformities in the CIS module. Otherwise, the magnitude of the corrected reflectance profiles generally remained unchanged. The remaining non-uniformities, which may be seen in the corrected profiles, are defects of the sampled object and are not from the signature lens imaging differences in diffuse versus specular lighting.

A processor provided within the CIS module or the printing device may be provided to both calibrate the CIS module and to process the reflectance data detected by the sensors. The above formulas may be implemented by machine readable executable instructions stored in a memory, which may be executed by the processor. The processor may be dedicated hardware like ASICs or FPGAs, software, or a combination of dedicated hardware and software.

In other implementations, the invention may be used for sensors, which imaging glossy paper, plastic substrates, or other diffuse surfaces, which may also suffer from diffuse non-uniformities when operating in specular mode.

While certain features have been described in connection with what is presently considered to be the most practical and preferred embodiment, it is to be understood that it is capable of further modifications and is not to be limited to the disclosed embodiment, and this application is intended to cover any variations, uses, equivalent arrangements or adaptations and including such departures from the present disclosure as come within known or customary practice in the art.

What is claimed is:

1. A method for calibrating a specular reflectance measurement sensor for use in a device, the method comprising:
   providing a sensor module, the sensor module comprising:
   (i) an illuminator configured to emit a beam of light at a target, thereby producing specular reflectance at an angle;
   (ii) a linear array sensor configured to detect that specular reflectance; and
   (iii) a processor configured to process the specular reflectance detected by the sensor;
   measuring a reflectance profile of a diffuse white reflecting surface using the sensor module and storing it in a memory;
   determining a non-uniformity correction factor which quantifies reflectance non-uniformity differences between a target and the diffuse white reflecting surface;
   measuring a specular reflectance profile of a target using the sensor module;
   determining a calibrated specular reflectance profile of the target based upon the pixel-wise non-uniformity correction factor, and
   providing the calibrated specular reflectance profile of the target to the device.

2. The method according to claim 1, wherein the target is a photoreceptor having toner on it.

3. The method according to claim 1, wherein diffuse white specular reflectance profile is measured prior to the sensor module being installed in the printing machine.

4. The method according to claim 1, wherein the target specular reflectance profile measurement is performed after the sensor module is installed in the printing machine.

5. The method according to claim 1, wherein the calibrated specular reflectance profile of the target is used to determined the density of the toner on a photoreceptor.

6. The method according to claim 1, wherein determining the calibrated specular reflectance profile of the target comprises:
   scaling the diffuse white specular reflectance profile with respect to a photoreceptor reflectance profile of a photoreceptor of the device; and
   scaling the pixel-wise non-uniformity correction factor based on the diffuse content of the reflected light.

7. The method according to claim 6, wherein the scaled diffuse white reflecting surface specular reflectance profile $(R^W_{PR})$ is determined, as follows:

$$R^W_{PR}(i) = [\text{WHITE}(i) - \text{DARK}(i)] / [PR(i) - \text{DARK}(i)] \times \frac{\overline{PR}}{\overline{\text{WHITE}}}$$

where:
   WHITE is the pixel-wise reflectance profile for the diffuse white reflecting surface;
   DARK is the pixel-wise reflectance profile for the photoreceptor having no light thereupon it;
   PR is the pixel-wise reflectance profile for the bare photoreceptor;
   $\overline{\text{WHITE}}$ is the mean value for WHITE; and
   $\overline{PR}$ is the mean value for PR.

8. The method according to claim 7, wherein the pixel-wise non-uniformity correction factor ($\delta R_W$) is determined, as follows:

$$\delta R_W(i) = 1 - R_{PR}^W(i).$$

9. The method according to claim 8, wherein scaling the pixel-wise non-uniformity correction factor comprises:
   (a) determining a pixel-wise solid area color reflectance profile ($R_S^C$) and a mean solid area color reflectance ($\overline{R_S^C}$) for each color c of a color scheme;
   (b) determining a toner area coverage reflectance profile ($R_{AC}^C$) for a test patch of that color C and a mean toner area coverage reflectance ($\overline{R_{AC}^C}$) for that test patch;
   (c) determining a diffuse to specular ratio, ($DSR^C$); and (d) determining a scaled pixel-wise non-uniformity correction factor ($\delta R_{AC}^C$), as follows:

$$\delta R_{AC}^C(i) = DSR^C \times \overline{R_S^C} \times \delta R_W(i).$$

10. The method according to claim 9, wherein the diffuse to specular ratio is determined, as follows:

$$DSR^C = \frac{1 - \overline{R_{AC}^C}}{1 - \overline{R_S^C}}.$$

11. The method according to claim 9, wherein the pixel-wise calibrated specular reflectance profile ($R'_m{}^C$) is determined for the target reflectance profile ($R_m^C$), as follows:

$$R'_m{}^C(i) = R_m^C(i) \times [1 + \delta R_{AC}^C(i)].$$

12. The method according to claim 1, wherein the target is a halftone cell.

13. The method according to claim 1, wherein the target is a test patch.

14. The method according to claim 1, wherein the diffuse white reflecting surface is a white resin sheet or a high quality sheet of white paper.

15. The method according to claim 1, wherein the sensor is capable of measuring the target specular reflectance profile though a selected portion of its width.

16. A computer readable media having stored computer executable instructions, wherein the computer executable instructions, when executed by a computer, directs a computer to perform a method for calibrating a specular reflectance measurement sensor for use in a printing machine; the method comprising:

providing a sensor module, the sensor module comprising:
  (i) an illuminator configured to emit a beam of light at a target, thereby producing specular reflectance at an angle;
  (ii) a linear array sensor configured to detect that specular reflectance; and
  (iii) a processor configured to process the specular reflectance detected by the sensor;

measuring a reflectance profile of a diffuse white reflecting surface using the sensor module and storing it in a memory;

determining a non-uniformity correction factor which quantifies reflectance non-uniformity differences between a target and the diffuse white reflecting surface;

measuring a specular reflectance profile of a target using the sensor module;

determining a calibrated specular reflectance profile of the target based upon the pixel-wise non-uniformity correction factor, and providing the calibrated specular reflectance profile of the target to the device.

\* \* \* \* \*